United States Patent [19]
Adachi et al.

[11] Patent Number: 5,351,198
[45] Date of Patent: Sep. 27, 1994

[54] QUANTITATIVE ANALYTICAL METHOD AND APPARATUS FOR DETERMINING A PLURALITY OF INGREDIENTS WITH SPECTROMETRIC ANALYSIS

[75] Inventors: Masayuki Adachi, Kyoto; Yutaka Yamagishi, Shiga; Kaori Inoue, Hirakata, all of Japan

[73] Assignee: Horiba, Ltd., Kyoto, Japan

[21] Appl. No.: 837,235

[22] Filed: Feb. 14, 1992

[51] Int. Cl.$^5$ .............................................. G01N 21/00
[52] U.S. Cl. ................... 364/498; 364/502; 356/319
[58] Field of Search .................. 364/498, 497, 502; 356/307, 312, 315, 319

[56] References Cited

U.S. PATENT DOCUMENTS

| | | | |
|---|---|---|---|
| 4,365,303 | 12/1982 | Hannah et al. | 364/498 |
| 4,660,151 | 4/1987 | Chipman et al. | 364/498 |
| 4,719,582 | 1/1988 | Ishida et al. | 364/498 |
| 4,801,805 | 1/1989 | Butler et al. | 250/343 |
| 4,974,209 | 11/1990 | Hoult | 364/497 |
| 5,046,846 | 9/1991 | Ray et al. | 356/326 |
| 5,116,122 | 5/1992 | Fukuma | 356/326 |

OTHER PUBLICATIONS

P. R. Griffith et al., "Fourier Transform Infrared Spectrometry", New York (1986) Chapter 10, "Quantitative Analysis", pp. 338 to 368.

W. Bruegel, "Einfuehrung in the Ultrarotspektroskopie", Darmstadt (1962), pp. 314 to 343 and pp. 370 to 393.

A. L. Smith, "Applied Infrared Spectroscopy", New York (1979), pp. 219 to 248.

*Primary Examiner*—Thomas G. Black
*Assistant Examiner*—Tan Q. Nguyen
*Attorney, Agent, or Firm*—Price, Gess & Ubell

[57] ABSTRACT

A quantitative analytical method with spectrometric analysis, wherein a sample is irradiated with light, and a plurality of ingredients contained in the sample to be measured are quantitatively determined on the basis of absorptivities at a plurality of appointed wave number points in an absorption spectrum obtained at that time. An assumed concentration-operating matrix is obtained from a combination of reference spectra for a plurality of ingredients, of which the concentrations have been known, and is previously prepared. The concentrations of the respective ingredients to be measured are calculated by the use of the concentration-operating matrix, thereby capable of carrying out a quantitative analysis in a short time with high accuracy.

12 Claims, 12 Drawing Sheets

QUANTITATIVE ANALYTICAL METHOD AND APPARATUS FOR DETERMINING A PLURALITY OF INGREDIENTS WITH SPECTROMETRIC ANALYSIS

BACKGROUND OF THE INVENTION

1. Field of the Invention

The present invention relates to a quantitative analytical method and apparatus for spectrometric analysis in which a sample is irradiated with radiation such as infrared light, and a concentration of a plurality of ingredients contained in the sample are measured on the basis of its absorptivities at a plurality of appointed wave number points across an absorption spectrum.

2. Description of Related Art

A Fourier transformation infrared spectrometer (hereinafter referred to as FTIR) 1 having a construction as shown in, for example, FIG. 11, has been used for quantitative analytical results. The FTIR 1 is composed of an analytical portion 2 and a data-treating portion 3 for processing an interferogram which is the output of the analytical portion 2.

The analytical portion 2 is further composed of a light source 4 constructed so as to emit parallel infrared beams, an interference mechanism 8 comprising a beamsplitter 5, a fixed mirror 6, and a movable mirror 7 movable in the X-Y direction, a cell 9 housing a sample to be measured therein and irradiated with the infrared beams from the light source 4 through the interference mechanism 8, and a detector 10 composed of a semiconductor detector and the like.

The data-treating portion 3 comprises a spectrum-operating portion 11 processing an absorption spectrum of data composed of, for example, a computer and a quantitative operating portion 12 capable of calculating concentrations of ingredients contained in the sample to be measured by applying Lambert-Beer's law to the calculated absorption spectrum.

In addition, the spectrum-operating portion 11 comprises an adding and averaging portion 13 for adding and averaging, for example, the data of the interferogram, a high-speed Fourier transforming portion 14, in which output data from the adding and averaging portion 13 are subjected to a high-speed Fourier transformation, and an operating portion 15 for carrying out a spectral operation to determine the ingredients to be measured on the basis of output data from the high-speed Fourier transforming portion 14.

In an FTIR 1 having the above-described construction, a reference sample and an unknown sample to be measured, are separately housed in the cell 9 in order to measure an interferogram of the reference sample and of the sample to be measured, respectively. These interferograms are subjected to a Fourier transformation to obtain a characteristic power spectra; that is, a spectra of beams which have been transmitted through the cell 9. A ratio of the power spectrum of the sample to be measured to the power spectrum of the reference sample is then determined. A value of this ratio is converted to an absorptivity scale to obtain the absorption spectrum of the sample.

In the quantitative operating portion 12, which is a latter stage of the data-treating portion 3, the concentrations of the ingredients contained in the sample to be measured can be calculated by applying Lambert-Beer's law to the calculated absorption spectrum. A display portion 16 can provide a visual indication of the concentrations of ingredients.

Problems have occurred in the prior art when the sample contains multiple ingredients which are to be simultaneously analyzed during a continuous measurement cycle. Additionally, when the amount of concentration of individual ingredients can vary widely, it is difficult to secure accurate readings. These problems frequently occur in the analysis of the by-products of combustion from vehicles.

Accordingly, a demand exists in the prior art to address these problems.

SUMMARY OF THE INVENTION

It is an object of the present invention to provide a quantitative analytical method to determine a plurality of ingredients in a simple and accurate analysis.

It is another object of the present invention to provide an analytical method to a plurality of ingredients by small-sizing a matrix used for a calculation of concentrations of the ingredients on the basis of an absorption spectrum while reducing the operation time.

It is still another object of the present invention to provide a quantitative analytical method to a plurality of ingredients capable of simply and accurately quantitatively analyzing a plurality of kinds of samples that are remarkably different in constituent ingredients.

In a first embodiment, an assumed concentration-operating matrix obtained from a combination of reference spectra for a plurality of ingredients, of which the concentrations have been known, are previously prepared, and concentrations of the respective ingredients to be measured are calculated by the use of the concentration-operating matrix.

In a second embodiment, a plurality of ingredients contained in the sample are classified into a plurality of groups of ingredients and frequency bands, used for a spectrometric analysis of the respective groups of ingredients, are classified into blocks for every group of ingredients.

In a third embodiment, groups of ingredients to be measured, characteristic of a plurality of samples to be measured, wherein the constituent ingredients can almost be estimated, are set in previously-appointed groups of wave number points for subsequent use in a calculation of ingredient concentration corresponding thereto, and one of the groups of wave number points for use in a calculation of concentration is selectively used to carry out the calculation of the concentration of the constituent ingredients of the respective samples to be measured.

In a fourth embodiment, suitable groups of ingredients to be measured and their concentration ranges are determined for a plurality of samples, where the expected constituent ingredients and concentration ranges can almost be estimated. Groups of wave number points are determined for use in a calculation of concentration for those combinations, and one of the groups of wave number points for use in a calculation of concentration is selectively used to carry out the calculation of concentrations.

According to the first embodiment, the concentration-operating matrix estimated from the ingredients to be measured is previously prepared, so that it is unnecessary to memorize the reference spectra of a plurality of ingredients in, for example, an analyzer. Moreover, it is not required to form the concentration-operating matrix within the analyzer, so that a quantitative analysis can be achieved in a short time and with high accuracy.

According to the second embodiment, a plurality of ingredients are classified into a plurality of groups of ingredients, and the frequency bands used for a spectrometric analysis of the respective groups of ingredients are classified into blocks for every group of ingredients, so that the matrix used for the calculation of concentration can be small-sized to simplify the operation. In addition, even in the case where the matrix is replaced midway in the operation, it is sufficient that only the matrix corresponding to the desired group of ingredients is replaced, so that any time loss required for replacement of the matrix can be reduced. Furthermore, the operation can be omitted for frequency bands of absorption spectra, which are not required for the calculation of concentration, so that the operation time can be further reduced.

According to the third and fourth embodiments, the groups of wave number points suitable to a plurality of kinds of samples to be measured, of which constituent ingredients are different, are appointed, so that interferential influences can be effectively canceled to achieve a highly accurate quantitative analysis. In particular, according to a method in which the groups of wave number points for use in a calculation of concentration exclusive for the combinations of the groups of ingredients to be measured and the concentration ranges are appointed, various considerations can be taken into account to establish a desired interference accuracy, as compared with a method in which the groups of wave number points for use in a calculation of concentration individually appointed for every ingredient to be measured (and concentration range) are combined later.

It is sufficient that the previously-appointed plurality of groups of wave number points for use in a calculation of concentration are memorized in a computer and can be used in a data-treating operation so that the FTIR interferometer itself is not changed in operation and construction. Therefore, the replacement of a group of wave number points for use in a calculation of concentration can be easily achieved by merely operating input keys. In summary, it is also possible that the suitable group of wave number points for use in a calculation of concentration (group of ingredients to be measured) is looked for while observing an output.

Consequently, according to the third and fourth embodiments, the ingredients in a plurality of kinds of samples can be accurately and simply quantitatively analyzed by using only one set of FTIRs.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a method and apparatus for spectrometric analysis.

To provide additional background, one of the present inventors has filed a Japanese Patent Application No. HEI2-274204, assigned to the present assignee on Oct.13, 1990, which discloses that relative absorptivities, which are the differences between local peak values and local valley values at a plurality of wave number points in an absorption spectrum, are summed up, and concentrations of the respective ingredients are separately obtained on the basis of spectra of the respective ingredients obtained from reference spectra of a plurality of ingredients. According to this method, the respective ingredients are individually analyzed on the basis of the spectra of the respective ingredients obtained by summing up the relative absorptivities, in a previously appointed range of a frequency spectrum, for every ingredient and the reference spectra for the respective ingredients, so that the respective ingredients can be quantitatively determined with high accuracy without being influenced by noises and interferences among the ingredients themselves.

However, in the case where a plurality of ingredients in a sample to be measured are quantitatively analyzed at the same time by the use of the above-described method, it is possible that the absorption spectra of a plurality of ingredients to be measured can be previously measured, and the measured absorption spectra can be memorized in, for example, a computer within an analyzer as reference spectra. In such a case, it is necessary to make a calibration matrix from the reference spectra within the computer each time that a plurality of ingredients of unknown concentrations in the sample to be measured are quantitatively determined.

However, in the above-described method of analyzing a plurality of ingredients, a linear algebraic method is employed on the basis of Lambert-Beer's law so that the absorptivity is proportional to the concentration of the ingredient to be measured. Lambert-Beer's law can be expressed as follows:

$$A(v) = C\alpha(v) \quad (1)$$

wherein C represents a concentration of an optional absorbent; $\alpha(v)$ represents an absorption spectrum of unit concentration at a wave number of $v$; and $A(v)$ represents an absorption spectrum of an absorbent of unknown concentration at a wave number of $v$.

Figure 12:
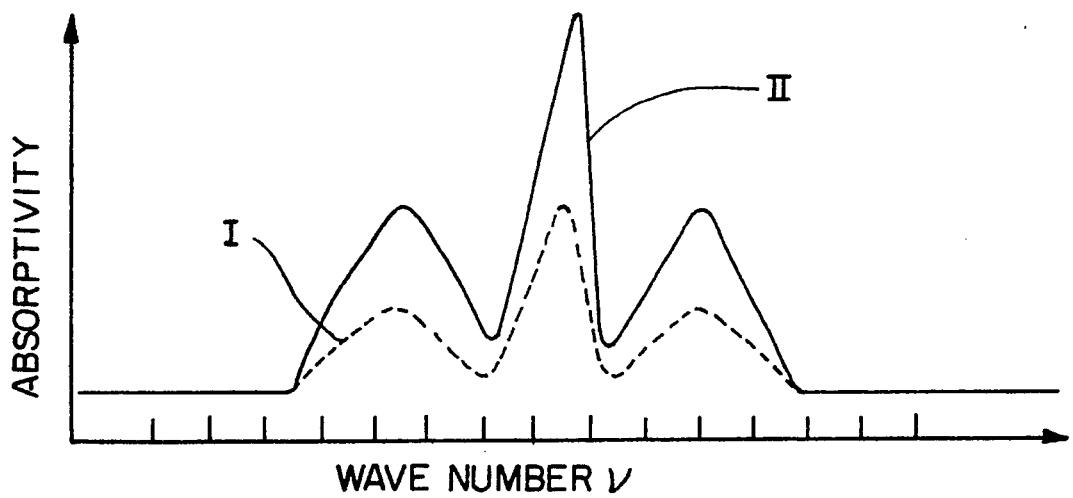
FIG. 12 is a diagram showing a general absorption spectrum for describing problems in the prior art.

This relationship is schematically shown in FIG. 12. Referring to FIG. 12, curve I and curve II show the absorption spectrum $\alpha(v)$ of unit concentration and the absorption spectrum of unknown concentration, respectively.

In the case where the absorptions of a plurality of ingredients are overlapped, the above-described formula (1) is expressed by the following merely linear combination (2):

$$A(v) = \Sigma_i C_1 \alpha_i(v) \quad (2)$$

wherein $C_1$ represents concentrations of the respective ingredients, and $\alpha_i(v)$ represents the absorption spectrum of unit concentration for the respective ingredients.

In a spectrometric analysis of a plurality of ingredients by the use of absorption spectra, which has been generally carried out, reference spectra $\alpha_i(v)$ for the respective ingredients are previously determined in a calibration stage to estimate the concentrations $C_i$ of the respective ingredients from the absorption spectrum $A(v)$ of an unknown mixture to be measured.

Usually, $A(v)$ is measured as a value corresponding to the continuous wave number points ranging, for example, from 4,000 cm$^{-1}$ to 400 cm$^{-1}$ in an infrared range, so that the formula (2) is expressed by the following simultaneous equations of the first degree (3):

$$A(v_j) = \Sigma_i C_i \alpha_i(v_j) \quad (3)$$

Accordingly, the concentrations of a plurality of ingredients can be estimated by carrying out an operation on these simultaneous equations of the first degree by the use of a matrix.

Figure 13:
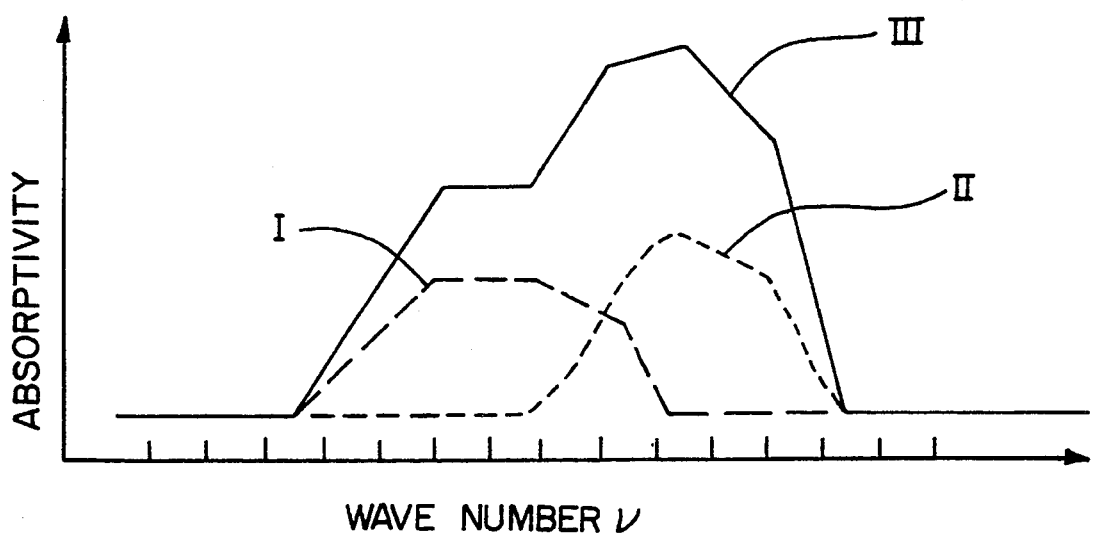
FIG. 13 is a diagram showing an overlap of schematic spectra of two ingredients.

FIG. 13 schematically shows absorption spectra of two ingredients overlapped. Referring to FIG. 13, curve I and curve II show an absorption spectrum of unit concentration $\alpha_1(v_j)$, $\alpha_2(v_j)$ for an ingredient gas, respectively, and curve III shows a linear combination of those spectra (shown above in Equation (3)).

However, in the above-described method, in the case where many kinds of ingredients are contained in the sample to be measured, a matrix used for an operation is excessively large-sized, and thus it becomes necessary to provide a large capacity memory for the computer. In addition, where it is required to transform the matrix midway in the operation, the operation of all ingredients is interrupted, so that problems have occurred in that time loss is increased.

When a plurality of ingredients in the sample to be measured are quantitatively analyzed by the use of the FTIR 1 having the above-described construction, if a large quantity of unexpected ingredients is contained in the sample to be measured, the calculated concentration values of the ingredients to be measured can be interrupted, according to circumstances. However, it is disadvantageous to analytical accuracy of other ingredients actually existing in the sample that the group of wave number points is appointed while erroneously expecting that the ingredients, which hardly exist in the sample to be measured, exist in high concentrations. Thus, it has been difficult to simply and accurately quantitatively analyze a plurality of kinds of samples to be measured that are greatly different in constituent ingredients.

Figure 1:
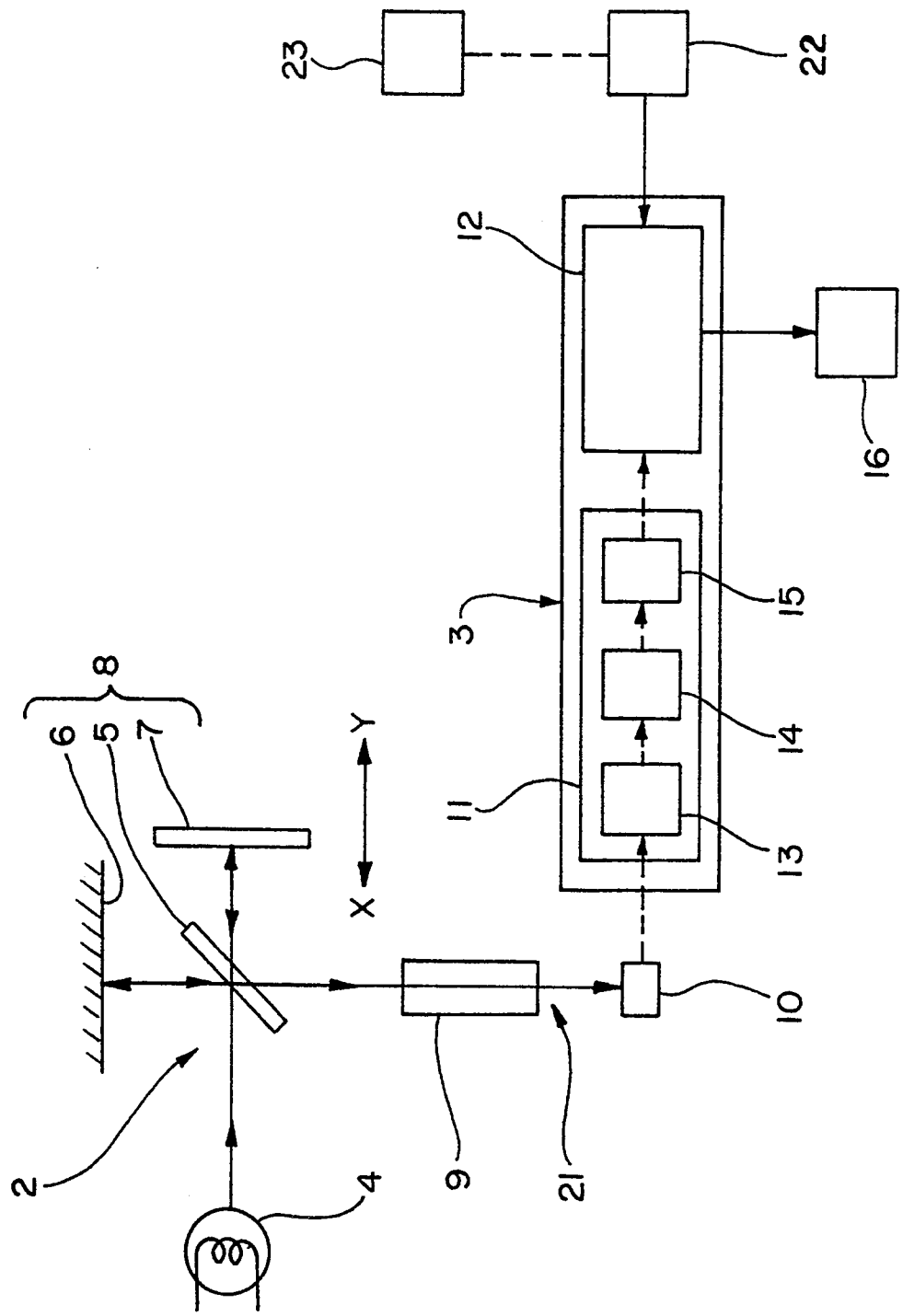
FIG. 1 is a drawing schematically showing one example of an FTIR for putting a method according to a first embodiment into practice.
Figure 11:
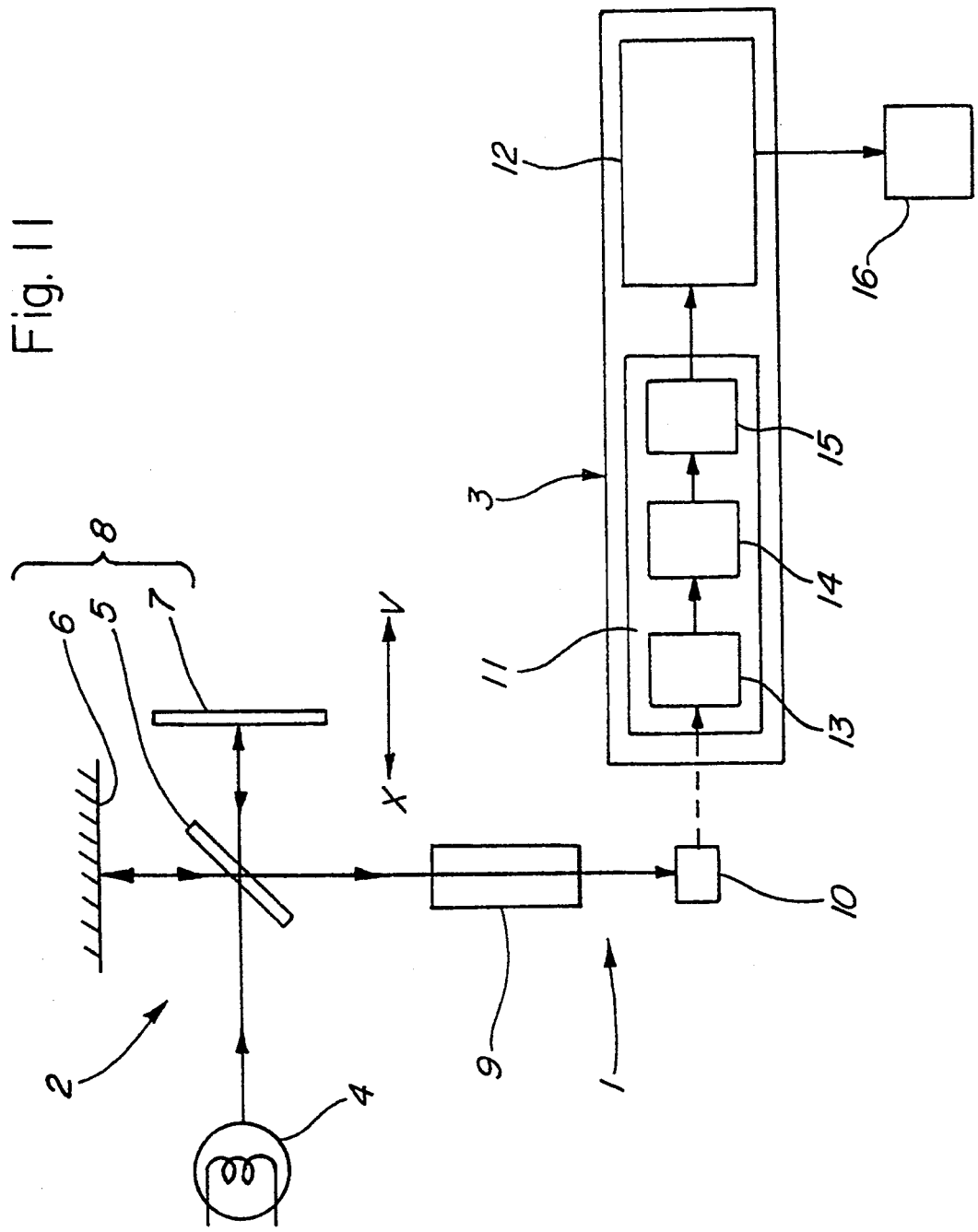
FIG. 11 a drawing showing a construction of a general FTIR.

FIG. 1 schematically shows an FTIR 21 as one example of an apparatus for performing a quantitative analytical method of a plurality of ingredients by the use of a spectrometric analysis. Referring to FIG. 1, the same elements as in FIG. 11 are designated by the same reference numerals.

Referring to FIG. 1, reference numeral 22 designates a memory portion for memorizing an assumed concentration-operating matrix $\Omega$ obtained from a combination of groups of referential spectra 23 for a plurality of ingredients of which concentrations have been known. In the memory portion 22, the groups of wave number points of optional gases (k kinds of gases), estimated from a composition of the ingredients to be measured, are appointed from the groups 23 of referential spectra $\alpha_m$ at m known concentrations to obtain the constituent spectrum $\Psi_k$ and then memorized as the assumed concentration-operating matrix $\Omega$ by the use of a compensation matrix.

In an FTIR 21 having the above-described construction, a reference sample or sample to be measured is housed in a cell 9 to measure an interferogram of the reference sample or the sample to be measured, respectively. The interferogram is subjected to a Fourier transformation to obtain a power spectrum; in short, a spectrum of light passing through said cell 9, and then a ratio of the obtained power spectrum of the sample to be measured to a power spectrum of a background; in short, a power spectrum in the absence of the sample to be measured, is obtained followed by transforming the obtained ratio to an absorptivity scale to obtain the absorption spectrum.

If, for example, three kinds of gases X, Y, Z are contained, the assumed concentration-operating matrix $\Omega$ by the referential constituent spectra put in the memory portion 22 is expressed by the following Equation (4):

$$\Omega = \begin{pmatrix} X_1 & Y_1 & Z_1 \\ X_2 & Y_2 & Z_2 \\ X_3 & Y_3 & Z_3 \end{pmatrix} \quad (4)$$

wherein $X_1$, $X_2$, $X_3$, $Y_1$, $Y_2$, $Y_3$, $Z_1$, $Z_2$, $Z_3$ represent a sum of the relative absorptivities for the kinds of gases X, Y, Z, respectively.

Also, the absorption spectrum of the gas, for which the concentration is unknown, can be obtained in the data-treating portion 3 in the same manner. In this case, a constituent spectrum $\Psi_u$ is expressed by the following Equation (5):

$$\Omega_u = \begin{pmatrix} X_4 \\ Y_4 \\ Z_4 \end{pmatrix} \quad (5)$$

wherein $X_4$, $Y_4$, $Z_4$ represent a sum of the relative absorptivities for gases X, Y, Z, respectively.

Equation (5) is rewritten by the use of a matrix to obtain the following Equation (6):

$$C = \Psi_u \Omega^{-1} \quad (6)$$

Here, C represents a vector comprising an unknown concentration and $\Psi$ represents a matrix with $\Omega_k$ as lines which is called a compensation matrix within a constituent spectrum range and is used as the assumed concentration-operating matrix here.

Accordingly, provided that a concentration of the gases X, Y, Z is $C_X$, $C_Y$, $C_Z$, respectively, the concentration of gases $C_X$, $C_Y$, $C_Z$; that is, a plurality of ingredients in the sample to be measured, can be simultaneously determined in an operating portion 12 by the following Equation (7):

$$(C_X, C_Y, C_Z) = \begin{pmatrix} X_4 & X_1 & Y_1 & Z_1 \\ Y_4 & X_2 & Y_2 & Z_2 \\ Z_4 & X_3 & Y_3 & Z_3 \end{pmatrix}^{-1} \quad (7)$$

In addition, the assumed concentration-operating matrix $\Omega$, exclusive for each combination of compositions of ingredients to be measured, may be formed to be memorized in the memory portion 22 so as to be optionally replaced at any time.

The case where the concentration of the respective ingredients is quantitatively determined by the use of an infrared absorption spectrum on an exhaust gas from a gasoline engine automobile as the sample is described as the second embodiment. Here, the respective ingredients are classified into three groups of ingredients A, B, C, as shown in the following Table I.

TABLE I

| | | Gaseous Ingredient | Wave Number Band (cm$^{-1}$) |
|---|---|---|---|
| Group | A | Hydrocarbons | 3,200 to 3,000 |
| of | B | $CO_2$, CO, $H_2O$, NO | 2,400 to 1,800 |
| ingredients | C | $NO_2$, $SO_2$, $CH_4$, $NH_3$ | 1,500 to 1,000 |

The ingredients of the above-described exhaust gas are $CO_2$, $SO_2$, $CH_4$, $NH_3$, $CO_2$, CO, $H_2O$, NO, and a group of hydrocarbons including $C_2H_2$, $C_2H_4$, and others.

The wave number ranges of the infrared absorption spectrum are limited as follows: a wave number range of 3,200 cm$^{-1}$ to 3,000 cm$^{-1}$ is adopted for the group of ingredients A, a wave number range of 2,400 cm$^{-1}$ to 1,800 cm$^{-1}$ for the group of ingredients B, and a wave number range of 1,500 cm$^{-1}$ to 1,000 cm$^{-1}$ for a group of ingredients C. These wave number ranges are set with reference to the absorption spectra of the individual ingredients contained in the respective groups.

A general linear algebraic method can be used as means for determining the concentrations of the respective ingredients contained in the group of ingredients in the exhaust gas.

The case where the concentrations of three ingredients are quantitatively determined by another method while generalizing the respective groups of ingredients as a group comprising three ingredients X, Y, Z is described.

First, a concept of a sum of relative absorptivities introduced into this method is described.

A spectrum output from the spectrometer generally contains noises resulting from various reasons and, accordingly, Equation (1) can be expressed by the following Equation (8):

$$A(v_i) = C\alpha(v_i) + \epsilon_i \quad (8)$$

wherein $\epsilon_i$ represents noises contained in the spectrum.

Paying attention to a difference between two optional points in the spectrum, Equation (8) can be expressed by the following Equation (9):

$$A(v_p) - A(v_b) = C[\alpha(v_p) - \alpha(v_b)] + \epsilon_p - \epsilon_b \quad (9)$$

wherein p, q represents a suffix showing the wave number points corresponding to a peak and a base of the spectrum, respectively. Thus, a relative absorptivity between such two points conforms to Lambert-Beer's law.

Usually, a spectrum of a substance, in particular, a spectrum of a gas containing many peaks and many pairs of wave number point $v_p$ of the peak and wave number point 98 $b$ of the base proper to a certain substance can be selected.

Figure 2:
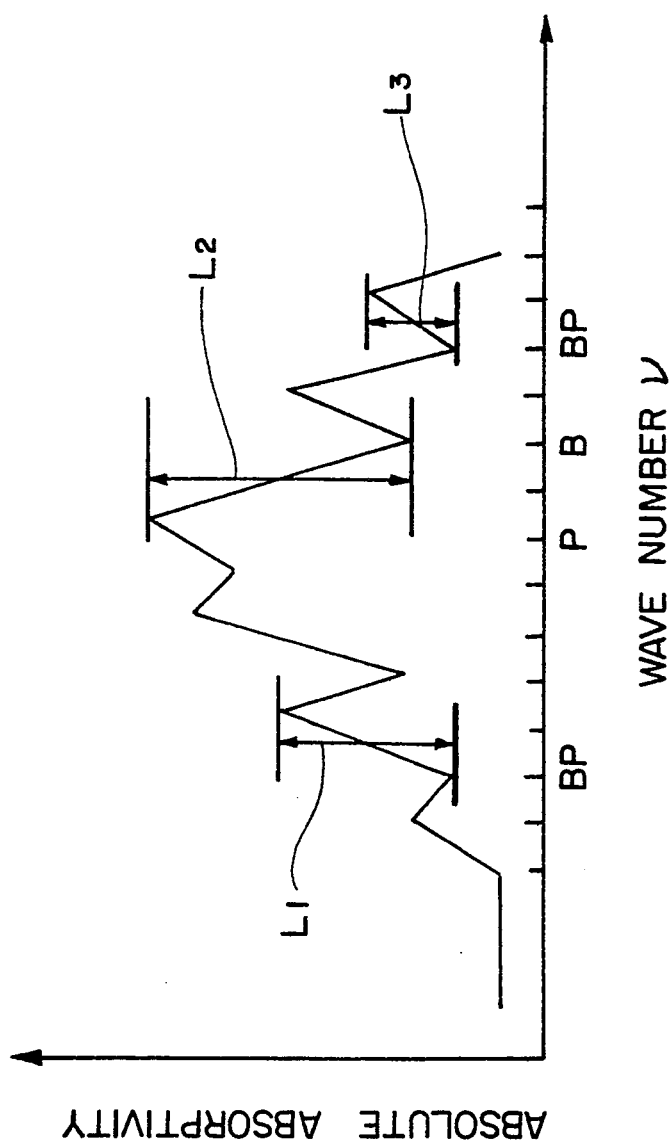
FIG. 2 is a diagram showing a schematic absorption spectrum of a gas and its relatively absorptivity for describing an operation used in one preferred method according to second embodiment.

FIG. 2 shows a schematic absorption spectrum of a gas and an example of relative absorptivities $L_1$, $L_2$, $L_3$ corresponding thereto. The respective relative absorptivities $L_1$, $L_2$, $L_3$ correspond to values of Equation (9).

Summing up these values, the following Equation (10) is obtained:

$$\Sigma_k[A(v_p) - A(v_b)]_k = C\Sigma_k[\alpha(v_p) - \alpha(v_b)] + \Sigma_k(\epsilon_p - \epsilon_b)_k \quad (10)$$

Equation (10) conforms to Lambert-Beer's law, and it can be found from Equation (10) that the second term on the right side averages random noises latent in the spectrum and cancels external turbulences such as a drift of a base line. Here, a value calculated by Equation (6) can be defined as an MAS (Multiple Absorption Sum) value.

The MAS value is expressed by the following Equation (11):

$$MAS = \Sigma_k[A(v_p) - A(v_b)]_k \quad (11)$$

In particular, the MAS value obtained for a reference spectrum of a single ingredient, of which the concentration has been known, is defined as the $MAS_i$ for the ingredient (i).

Figure 3:
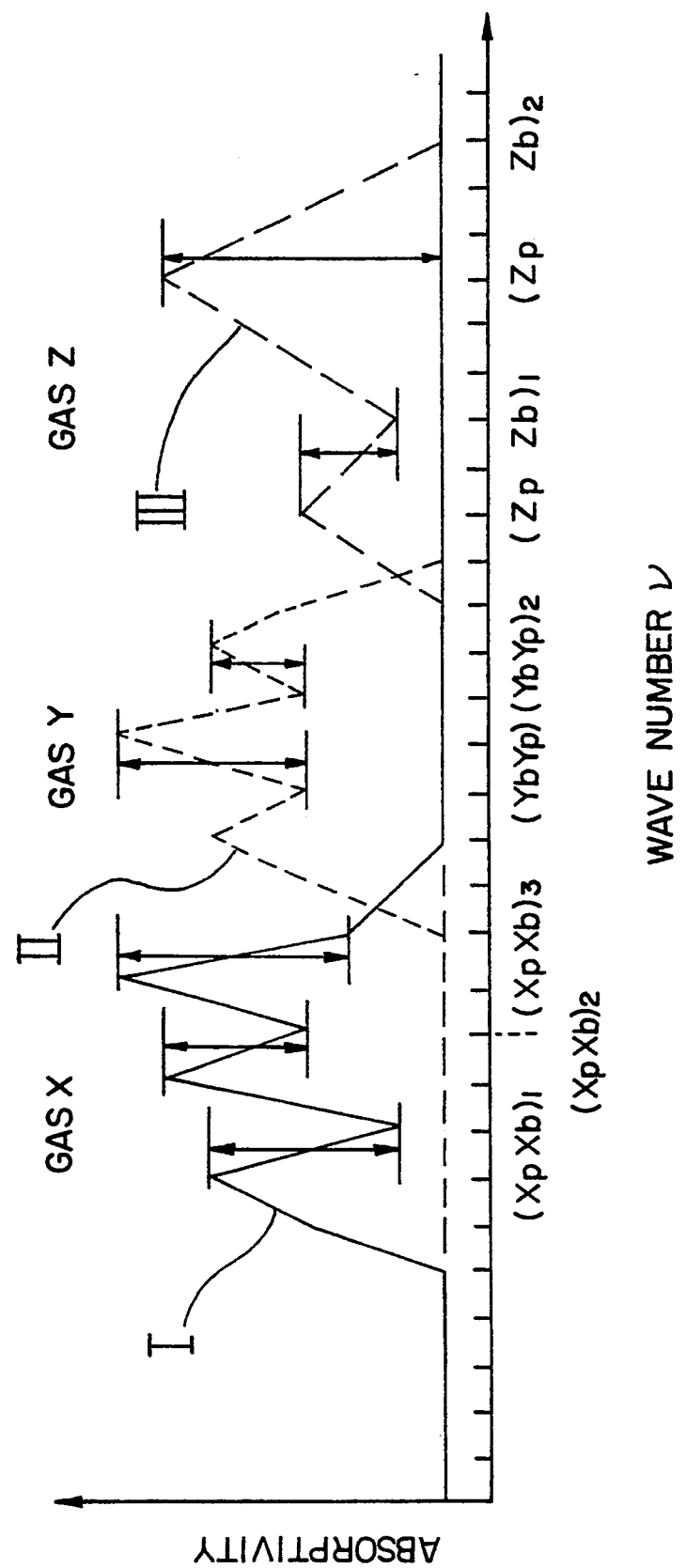
FIG. 3 is a diagram showing an example of wave number points appointed for different kinds of gases for generalizing groups of ingredients in a preferred embodiment.

FIG. 3 shows examples of the appointed wave number points for three kinds of gases contained in the above-described generalized group of ingredients. Referring to FIG. 3, curves I, II, and III show a reference spectrum of the gases X, Y, Z, respectively. A set of wave number points for the gas $X\Phi_x$: $(X_p, X_b)_k$, a set of wave number points for the gas $Y\Phi_y$: $(Y_p, Y_b)_k$, and a set of wave number points for the gas $Z\Phi_z$: $(Z_p, Z_b)$ are appointed, respectively. It is preferable that these pairs of peak and base are appointed so that an absorptivity, as large as possible, can be obtained and any influence by mutual absorptions will not be given.

An operation, in which a set of the above-described values of the appointed wave number points for m ingredients is defined as $\Phi_i$ (i=1 to m) and the set of pairs of peak and base of the ingredient (i) for one absorption spectrum is calculated by Equation (10), is defined by the following Equation (12):

$$\Sigma_k[A(\nu_p) - A(\nu_b)] = A \odot \Phi_i \tag{12}$$

wherein represents a new operator. This equation gives the MAS value.

Accordingly, the following Equation (13) is obtained:

$$MAS_i = A \odot \Phi_i \tag{13}$$

Thus, m values of $MAS_i$ are calculated for m values of $\Phi_i$. Provided that the $MAS_i$, which is a set of m numerals, is $\Psi$, it can be assumed that $\Psi$ is a spectrum having m elements.

$$\Psi = (MAS_i; i=1 \text{ to } m) \tag{14}$$

This new spectrum range (constituent spectrum range) can be graphically indicated with the kind of gas (i) as an axis of abscissa and the sum of relative absorptivities $MAS_i$ as an axis of ordinate. Accordingly, it can be assumed that Equation (9) was obtained by transforming the spectrum A into the constituent spectrum $\Psi$ by the use of the set $\Phi$.

Figure 4:
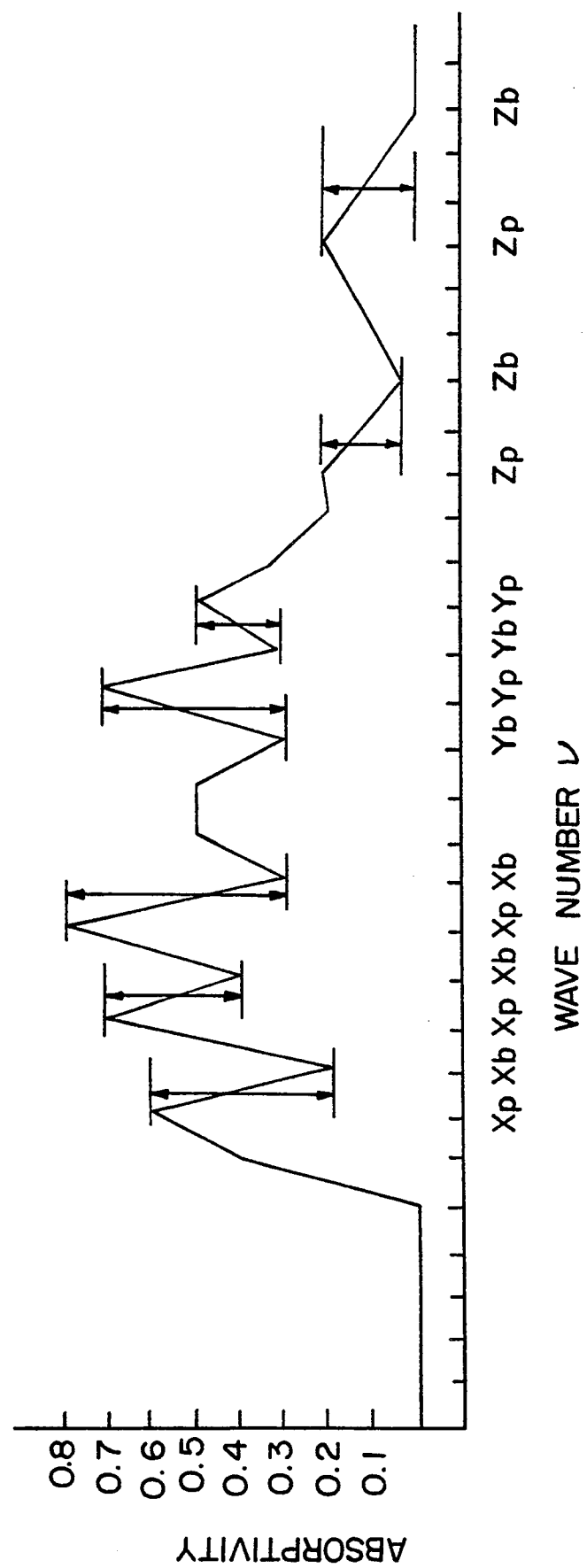
FIG. 4 is a diagram showing an absorption spectrum of generalized groups of ingredients in the above-described preferred embodiment.

This is described while applying the above generalizedly-shown group of ingredients as follows: FIG. 4 shows an absorption spectrum of a mixture comprising three kinds of gases X, Y, Z shown in FIG. 3 in an optional concentration, respectively; in short, an absorption spectrum of the whole above-generalized group of ingredients. The appointed values of wave number points for the respective pairs of peak and base of three kinds of gases appointed in FIG. 3 are applied to the absorption spectrum to determine the sum of the respective relative absorptivities expressed by X, Y, and Z, respectively, as shown in FIG. 4. These sums of the relative absorptivities can be plotted within a range, where an axis of abscissa represents the kind of gas and an axis of ordinate represents the sum of the relative absorptivities, as shown in FIG. 5.

For the constituent spectrum obtained in the above-described manner, an influence by noises is remarkably eliminated, and interferential influences among the spectra of different kinds of gases themselves are suppressed, as described above. If a transformation without being interfered among the ingredients themselves is possible, as shown in FIGS. 4 and 5, then the respective sums of the relative absorptivities are proportional to the concentrations of the respective ingredients within the constituent spectral range, so that the concentrations of the respective ingredients can be directly obtained.

Figure 5:
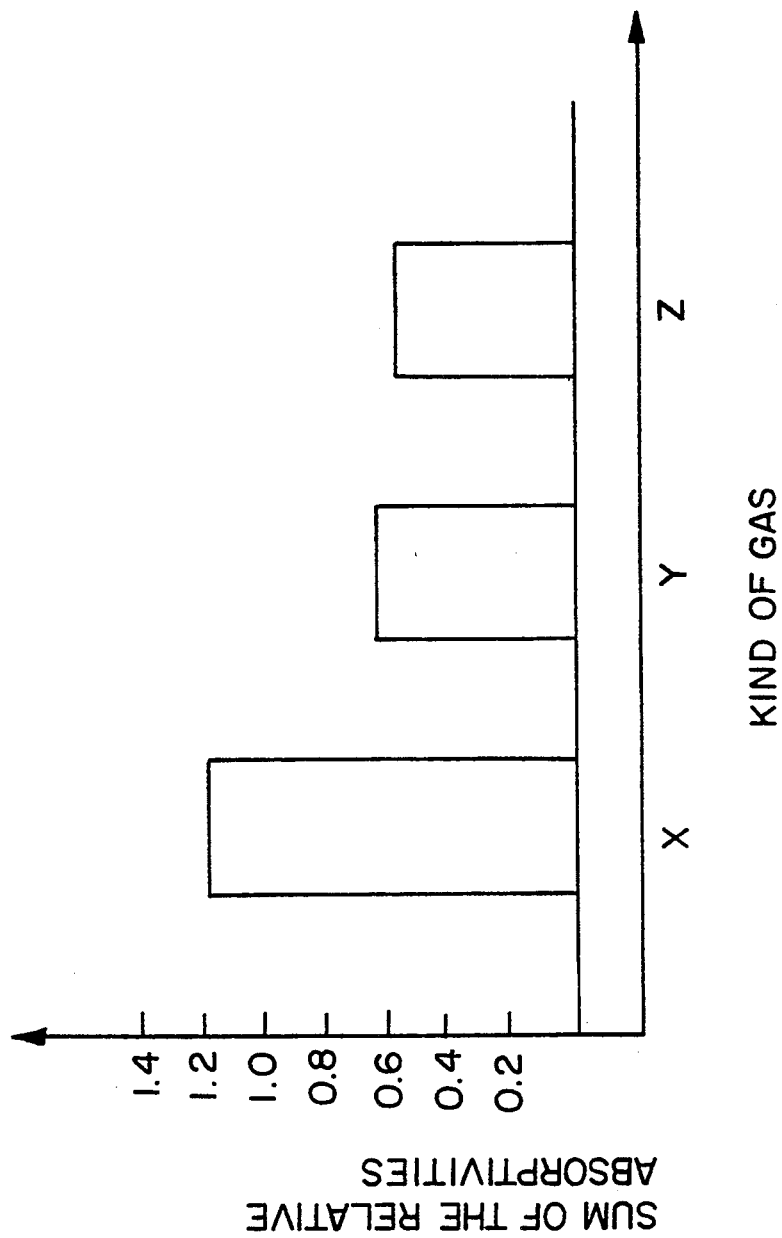
FIG. 5 is a diagram showing one example of a constituent spectrum calculated from an absorption spectrum of the generalized groups of ingredients in the above-described preferred embodiment.

However, the wave number points can hardly be predetermined by the operator without being interfered differently from those in FIGS. 4 and 5 in an actual absorption spectra of gases, so that the interferences are also left in the constituent spectral range after being transformed to some extent. In a quantitative analysis using the constituent spectral range, it is necessary to compensate the above-described interferences to some extent. Thus, the following treatment is divided into two steps, a compensation step preparing a matrix used for compensating interferences (compensation matrix) (that is, a step of preparing data for compensating interferences), and an estimation step for calculating unknown concentrations by the use of the data for compensating for the interferences.

In a compensation step, the compensation matrix is prepared as follows: generalizing for a case where there are reference spectra $\alpha_i$ (i=1 to m) of unit concentration for m ingredients, constituent spectra $\Psi_i$ (i=1 to m) corresponding to $\alpha_i$ can be obtained by applying the above-described set $\Phi_i$ of the appointed values of the wave number points to these reference spectra followed by carrying out a transformation expressed by the above-described Equation (13). The constituent spectra $\Psi_i$ can be obtained by calculating a sum of the relative absorptivities with a plurality of gases as a single sample, respectively.

Figure 6A:
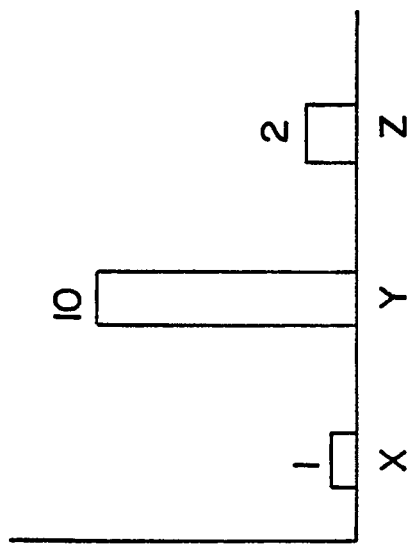
FIG. 6 is a diagram showing a referential constituent spectrum corresponding to the generalized groups of ingredients in the above-described preferred embodiment.
Figure 6B:
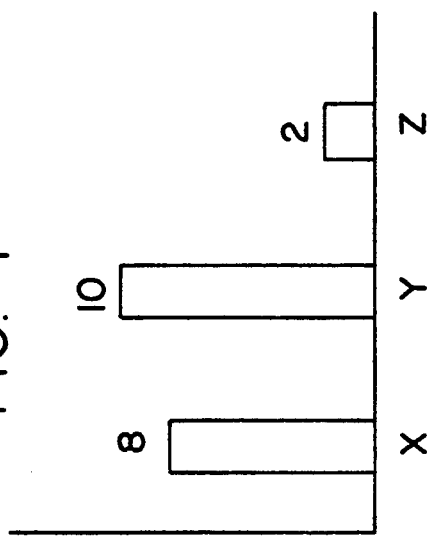
Figure 6C:
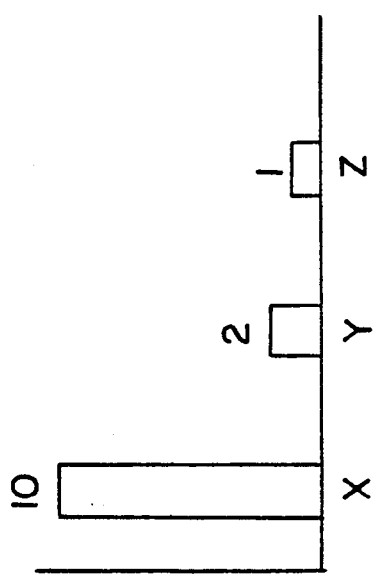

FIGS. 6(A), (B), and (C) show reference constituent spectra for three kinds of gases X, Y, Z contained in the group of ingredients. The compensation matrix in this case is expressed as follows:

$$\begin{pmatrix} 10 & 2 & 1 \\ 1 & 10 & 2 \\ 1 & -1 & 10 \end{pmatrix}$$

Figure 7:
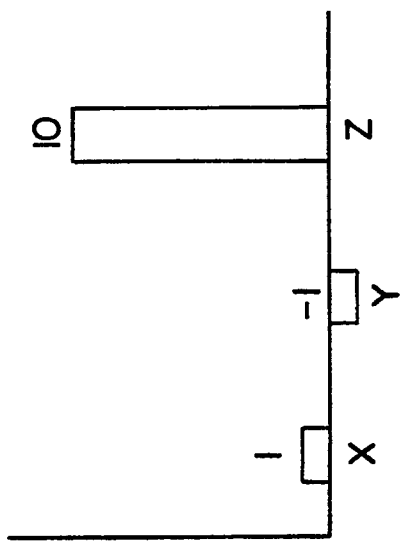
FIG. 7 is a diagram showing a constituent spectrum calculated from an absorption spectrum of a sample to be measured in the above-described preferred embodiment.
Figure 7:
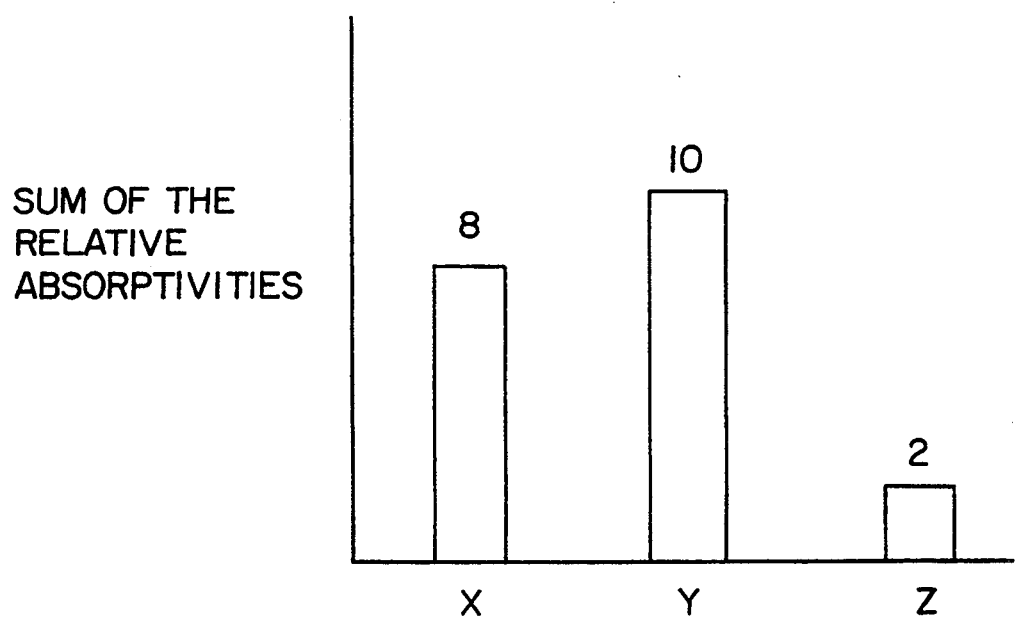

On the other hand, the constituent spectra of the group of ingredients can be obtained as shown in FIG. 7 from the absorption spectra obtained by spectro-metrically analyzing the sample to be measured within the wave number range assigned to the group of ingredients. The constituent spectra $\Psi_u$ in this case are expressed as follows:

$$\psi_u = \begin{pmatrix} 8 \\ 10 \\ 2 \end{pmatrix}$$

As for a general mixture gas comprising m kinds of gaseous ingredients (i=1 to m), provided that the unknown concentrations of the respective gaseous ingredients are $C_i$ (i=1 to m), $\Psi_u$ is expressed by a linear combination of $\Psi_i$. In short, the following Equation (15) always holds good.

$$\Psi_u = C_1 \cdot \Psi_1 + C_2 \cdot \Psi_2 + \ldots + C_m \cdot \Psi_m \tag{15}$$

Equation (15) can be rewritten by the use of a matrix to obtain the following Equation (16):

$$\Psi_u = C\Omega \tag{16}$$

Here, C represents a vector consisting of the unknown concentrations, and $\Omega$ represents a matrix with $\Psi_i$ as lines, which is called the compensation matrix within the constituent spectral range.

Accordingly, provided that the unknown concentrations of three kinds of gases X, Y, Z in the group of ingredients are $C_X$, $C_Y$, $C_Z$, the following Equation (17) holds good:

$$(C_X, C_Y, C_Z) \begin{pmatrix} 10 & 2 & 1 \\ 1 & 10 & 2 \\ 1 & -1 & 10 \end{pmatrix} = \begin{pmatrix} 8 \\ 10 \\ 2 \end{pmatrix} \quad (17)$$

In the compensation step, it is necessary to determine $\Omega$ to a high accuracy. In addition, as already described, $\Psi_i$ is a vector having a high linear independency; that is, being subjected to interferences to only a reduced extent, so that $\Omega$ is a matrix capable of obtaining a stabilized reverse matrix. Then, in the estimation step, the unknown concentrations can be estimated by solving Equation (16) on C; that is, calculating C from $C = \Psi_u \Omega^{-1}$.

As for Equation (17), $C_X$, $C_Y$, and $C_Z$ can be calculated from the following Equation (18), respectively:

$$(C_X, C_Y, C_Z) = \begin{pmatrix} 8 \\ 10 \\ 2 \end{pmatrix} \begin{pmatrix} 10 & 2 & 1 \\ 1 & 10 & 2 \\ 1 & -1 & 10 \end{pmatrix}^{-1} \quad (18)$$

The reverse matrix calculated here has a high linear independency of $\Omega$, so that a stabilized solution can be obtained. Accordingly, errors resulting from a numerical calculation of the estimated concentrations are remarkably reduced.

The concentrations of the individual ingredients contained in the respective groups of ingredients; in short, all ingredients contained in the sample to be measured, can be quantitatively determined by applying the above-described method to every group of ingredients A, B, C.

In this case, the above-described operation is carried out by dividing into respective groups of ingredients, so that a number of ingredients contained in the respective groups of ingredients is reduced and the matrix used in the operation can be small-sized, and thus the operation can be simplified. Moreover, the wave number ranges used for the respective groups of ingredients are not all within the infrared range, but the limited ranges divided into blocks for every group of ingredients are assigned. Thus, it is sufficient that the operation is carried out only for the limited ranges. Also, the time required for the operation can be reduced.

Furthermore, where, for example, the concentrations of the ingredients contained in one group of ingredients are higher than those estimated at the beginning, and the absorption spectra at the selected wave number points which cannot be held within the measurable range occurs midway through the operation, other wave number points must be appointed so that the absorption spectra may be held within the measurable range to carry out the operation. In this case, the above-described matrix must be replaced so as to correspond to the new wave number points, and processing time is required for such a replacement of the matrix.

However, here the spectrometric analysis is carried out by dividing the ingredients into a plurality of groups of ingredients, so that the operation is limited to the specified groups of ingredients to increase efficiency.

Next, another preferred embodiment, in which ingredients contained in an exhaust gas from a methanol-fueled automobile (hereinafter referred to as an exhaust gas), are quantitatively determined, is described.

Figure 8:
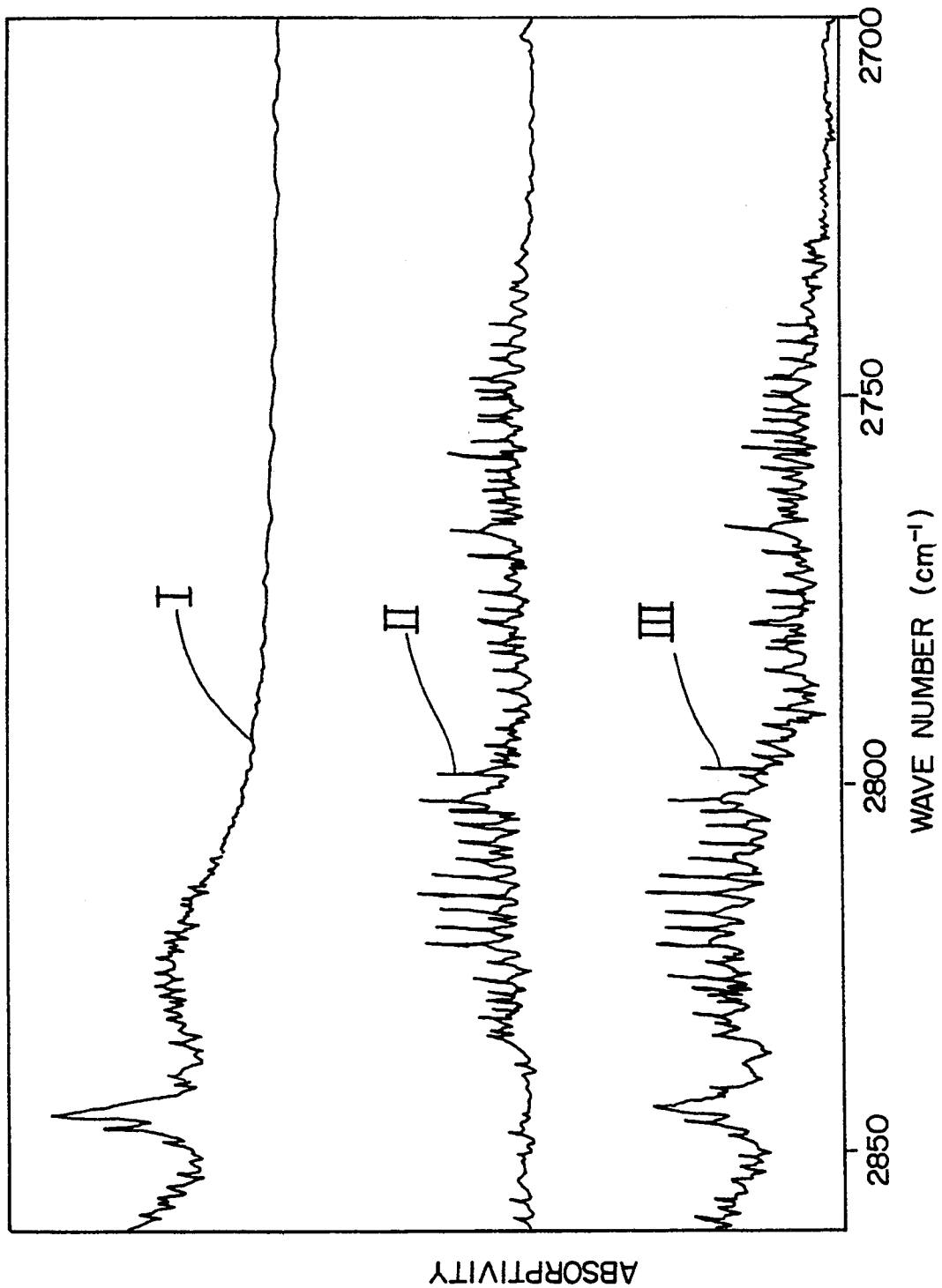
FIG. 8 is a diagram showing an absorption spectrum and a referential spectrum of one group of ingredients in the above-described preferred embodiment.

FIG. 8 shows an absorption spectrum obtained by means of the FTIR 1 shown in FIG. 1. Referring to FIG. 1, I shows a reference spectrum resulting only from methanol having a concentration of 103.7 ppm, II shows a reference spectrum resulting only from formaldehyde having a concentration of 26.4 ppm, and III shows an absorption spectrum of the exhaust gas. Referring to FIG. 8, an optional scale is used for an axis of ordinate to indicate an absorptivity.

As obvious from FIG. 8, the absorption spectrum III of the exhaust gas is overlapped with the reference spectrum I of methanol and the reference spectrum II of formaldehyde. That is, no absorption by other gaseous ingredients which could be contained in the same exhaust gas exists within the absorption wave number band; in short, the wave number range of the absorption spectrum of 2,850 cm$^{-1}$ to 2,700 cm$^{-1}$.

As a result, in the quantitative determination of the ingredients contained in this exhaust gas, two ingredients, methanol and formaldehyde, are discriminated from the other ingredients as one group of ingredients, and the spectrometric analysis of this group of ingredients is carried out within the above-described limited wave number range of 2,850 cm$^{-1}$ to 2,700 cm$^{-1}$.

In operation, the method described in the preceding preferred embodiment may be used, or the estimation may be carried out by a linear algebraic method, such as the least squares method, to convert the ratio into the actual concentration value by the use of the concentration data of the reference spectra.

As for the remaining group of ingredients discriminated from the above-described two ingredients, their concentrations can be quantitatively determined in the same manner. As for the exhaust gas from a methanol-fueled automobile, actually the above-described concentrations of two ingredients, methanol and aldehyde, have been regarded as particularly serious in view of toxicity, and the quantitative determination of the concentrations of other ingredients has not been regarded as serious. Accordingly, the quantitative determination of the exhaust gas can be considered substantially completed only by the quantitative determination of the concentrations of the above-described two ingredients.

Accordingly, it is unnecessary to carry out a measurement of, for example, the whole absorption wave number range (4,000 cm$^{-1}$ to 400 cm$^{-1}$) of the absorption spectrum and, thus, the treatment time can be reduced.

The third and fourth embodiments will be described below. These embodiments are considerably different from conventional methods, in that suitable groups of ingredients to be measured and concentration ranges are set up for a plurality of kinds of samples to be measured. The constituent ingredients and concentration ranges can almost be estimated, to previously appoint groups of wave number points for use in a calculation of concentration consisting of a plurality of wave number points exclusive for those combinations. The respective exclusive groups of wave number points for use in a calculation of concentration also being appointed for samples to be measured, of which other different constituent ingredients can be estimated. The group of wave number points for use in the calculation of concentration is predetermined, depending upon the expected composition of the sample (this is useful where known ingredients can be expected to be formed, such as in an engine exhaust). These groups of wave number points can be stored in the memory of the data-treating portion 3 and, in an analysis, groups of wave number points for use in a calculation of concentration corresponding to the combinations of the groups of ingredients to be measured and the concentration ranges suitable for the sample to be measured are selectively used to carry out the calculation of concentration. Even though the same ingredient is contained at concentrations within the same range, the same wave number point is not always used for the calculation of concentration of that ingredient.

Figure 9:
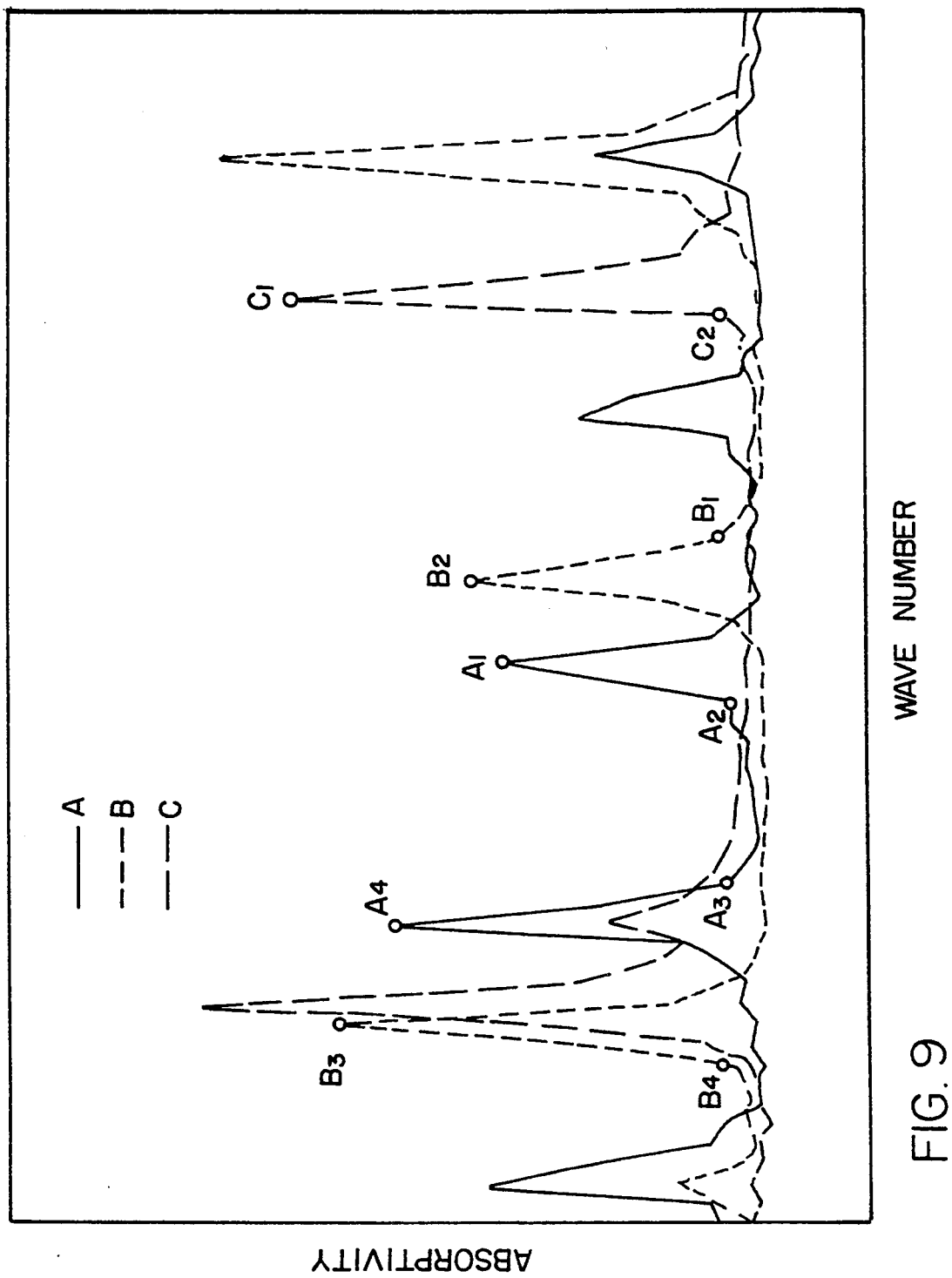
FIG. 9 is a diagram showing one example of an absorption spectrum used for describing methods according to third and fourth embodiments.

Assuming that compounds A, B, C have absorption spectra as shown in FIG. 9, one example of a method of selecting the wave number points for use in a calculation of concentration exclusive for the sample to be measured and different in composition from compounds A, B, C is shown in Table II.

TABLE II

|  | Pattern ① Merely A and B | Pattern ② A, B, and C (C: low concentration) | Pattern ③ A, B, and C (C: high concentration) |
| --- | --- | --- | --- |
| For the calculation of A | $A_3\ A_4$ | $A_3\ A_4$ | $A_1\ A_2$ |
| For the calculation of B | $B_3\ B_4$ | $B_1\ B_2$ | $B_1\ B_2$ |
| For the calculation of C | — | $C_1\ C_2$ | $C_1\ C_2$ |

As shown in Table II, patterns ②, ③, containing compound C as an object to be measured, show that a great absorption of compound C is avoided, so that patterns ②, ③ are different from pattern ①, in which compound C is not taken into consideration in the wave number point for use in a calculation of the concentration of compound B. Also, patterns ②, ③ are the same in concentration range as compounds A, B, but different only in concentration from compound C. An estimated concentration of compound C is different, so that the wave number point for use in a calculation of the concentration of compound A is differently appointed. In addition, even though the ingredients to be measured or their concentration ranges are different, as in patterns ① and ② or patterns ② and ③, a partial number of the same wave number points may be used. In addition, although the group of wave number points for use in a calculation of the concentration of compound C in patterns ②, ③ is the same in this example, actually the group of wave number points may be used properly depending upon the concentration range.

In the above-described manner, the patterns of the wave number points for use in a calculation of concentration exclusively for the ingredients to be measured, or the combinations of ingredients to be measured and the concentration ranges, respectively, are appointed, and these patterns are memorized in the memory of the data-treating portion 3 so as to be optionally replaced, as the occasion requires.

The specific selection of wave number points, in a quantitative determination, is based on a sufficient difference between corresponding peak values and valley values to be effective in providing a characteristic absorption of an ingredient. The specific set of wave numbers to constitute a measurement range can vary with the expected level of concentration of one or more ingredients.

However, in cases where the ingredient in the sample to be measured is quantitatively determined by the use of the FTIR, the concentration range, where the concentration can be accurately calculated, of a certain group of wave number points for use in the calculation of concentrations, is comparatively narrow. In short, a high concentration cannot be correctly analyzed by using a group of wave number points for use in the calculation of low concentration, while a low concentration cannot be detected by using a group of wave number points for use in the calculation of high concentration, due to a deterioration of a minimum detecting sensitivity.

However, wave number points at which the optical absorptivity is too high cannot be used, because not only is error increased, but also a linearity characteristic is diminished. Basically, as used herein, the term "linearity" refers to a sufficient proportional relationship between the optical absorption coefficient A at a certain wave number point and a sample concentration C, such as $A \cong K \times C$, where K is a constant.

In addition, the wave number points at which an absorption by the interferential ingredients is increased should also be avoided as far as possible. The wave number points to be used can also be determined by incorporating other conditions, such as the size of the matrix obtained.

As understood from the above description, a necessary and sufficient consideration is taken differently for the interferential ingredients from the method in which the wave number points used for the calculation of concentration of the respective ingredients. For example, wave number points $A_1$, $A_2$ for compound A, wave number points $B_1$, $B_2$ for compound B, and wave number points $C_1$, $C_2$ for compound C, are previously appointed, and they are combined, depending upon the constituent ingredients of the sample to be measured. Thus, a plurality of samples to be measured, which are greatly different in constituent ingredients, can be quantitatively analyzed with high accuracy by using only one set of FTIRs.

Figure 10:
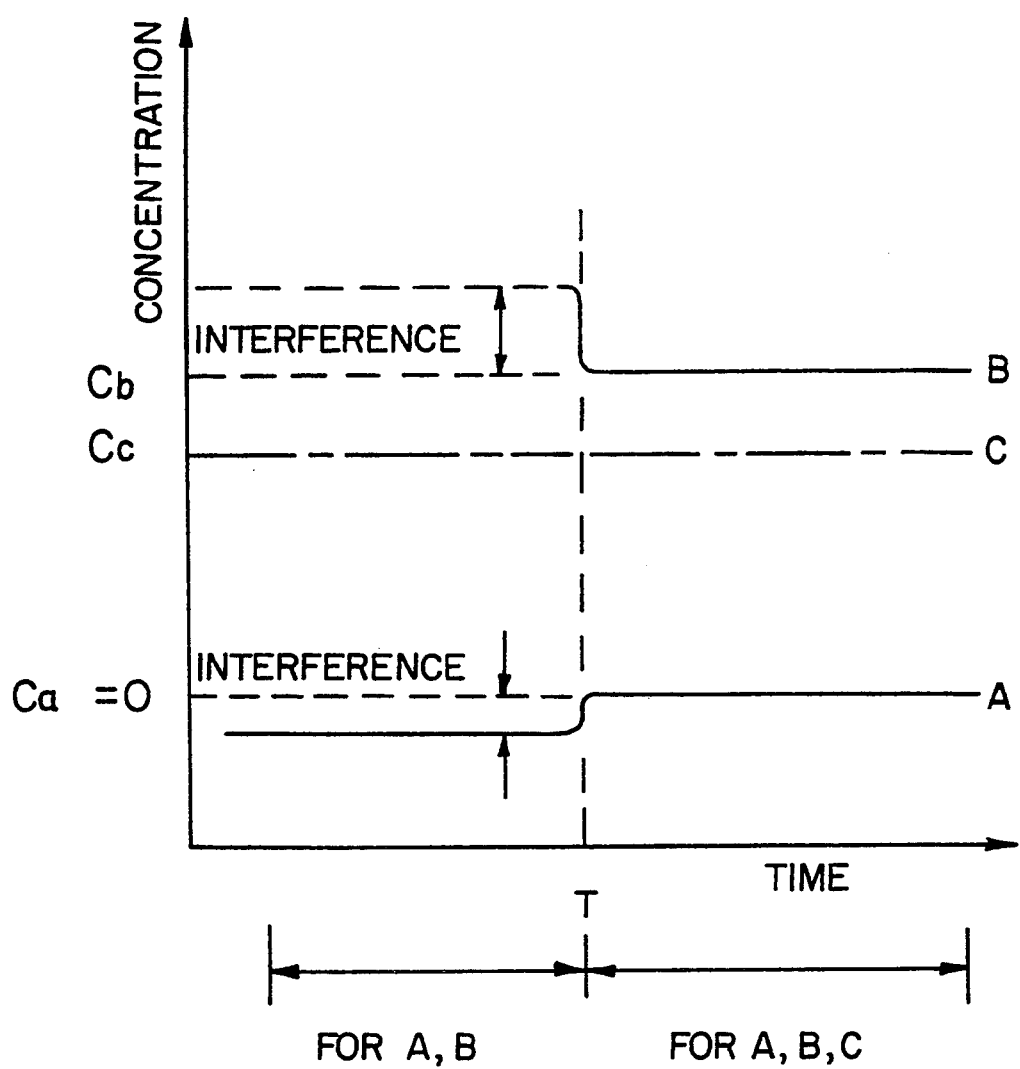
FIG. 10 is a diagram showing one example of an output wave shape.

FIG. 10 shows an example of continuous outputs in which, if the sample to be measured containing compound C is calculated by the use of a group of wave number points for calculation of concentration of two ingredients, compounds A, B, not taking compound C into consideration, interferences are produced. However, if the group of wave number points for use in a calculation of two ingredients, compounds A, B, is replaced with the group of wave number points for use in a calculation of three ingredients, compounds A, B, C, at a time T, then correct measured values can be obtained. Referring to FIG. 10, $C_a$, $C_b$, and $C_c$ designates the actual concentration of compounds A, B, and C ($C_a$ is zero), respectively.

In addition, it is not necessary that the apparatus for applying the method according to the second to fourth embodiments have the same construction as the apparatus for putting the method according to the first embodiment into practice; that is, they may have the same construction as shown in, for example, FIG. 11. In addition, apparatus other than the FTIR may be used as means for obtaining the absorption spectrum in the above-described preferred embodiments.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A quantitative analytical method of using spectrometric analysis, in which a sample is irradiated with light, and a plurality of ingredients contained in the sample to be measured are quantitatively determined on the basis of absorptivities at a plurality of appointed wave number points in an absorption spectrum obtained at that time, comprising:

establishing groups of ingredients to be measured suitable to a plurality of kinds of samples to be measured, those groups having ingredients which can be approximately estimated;

determining groups of wave number points corresponding to the respective groups of ingredients;

storing the groups of wave number points;

measuring the value of a sample across an absorption spectrum containing the groups of wave number points;

using one of the groups of wave number points to calculate the concentration of the values of the ingredients in the sample;

determining if the calculated concentration of ingredients is appropriate for the group of wave number points used and if not, selecting a different group of stored wave number points until the appropriate group of wave number points is used to calculate the concentration of the ingredients; and providing the concentration of the ingredients.

2. A quantitative analytical method as set forth in claim 1, wherein the sample to be measured is an exhaust gas from a methanol-fueled automobile, and formaldehyde and methanol in the exhaust gas are discriminated from other ingredients as one group of ingredients within an absorption spectrum wave number range of 2800 cm$^{-1}$ to 2700 cm$^{-1}$.

3. A quantitative analytical method as set forth in claim 1 wherein each group of wave number points correspond to a peak value of absorptivity and a base value for specific wave numbers.

4. A quantitative analytical spectrometric method of measuring a sample of exhaust gas on the basis of an absorption spectrum obtained to determine the concentration of formaldehyde and methanol, comprising the steps of:

determining concentration ranges for various combinations of formaldehyde and methanol;

determining frequency bands, used for a spectrometric analysis of formaldehyde and methanol for each various combination within an absorption wave number range of 2800 cm$^{-1}$ to 2700 cm$^{-1}$;

storing the frequency bands and absorption wave number corresponding to each combination of formaldehyde and methanol;

measuring the value of a sample across an absorption spectrum of the stored frequency bands; and using one of the frequency bands and the corresponding absorption wave numbers stored to calculate the concentration of formaldehyde and methanol.

5. A quantitative analytical spectrometric method as set forth in claim 4 further including determining if the calculated concentrations of formaldehyde and methanol is appropriate for the absorption wave numbers of the concentration range and if not, selecting different frequency bands and absorption wave numbers until the appropriate frequency bands and absorption wave numbers are used to calculate the concentration of the formaldehyde and methanol and providing the concentrations.

6. A quantitative analytical method of using spectrometric analysis, in which a sample is irradiated with light, and a plurality of ingredients contained in the sample to be measured are quantitatively determined on the basis of absorptivities at a plurality of appointed wave number points in an absorption spectrum obtained at that time, comprising:

establishing groups of ingredients to be measured suitable to a plurality of kinds of samples to be measured, those groups having ingredients which can be approximately estimated;

determining groups of wave number points corresponding to the respective groups of ingredients;

storing the groups of wave number points;

determining a corresponding compensation data for each group of wave number points;

storing the corresponding compensation data to compensate for any interference between ingredients;

obtaining the value of a sample across an absorption spectrum containing the groups of wave number points;

using one of the groups of wave number points to calculate the concentration of the values of the ingredients in the sample; and using a corresponding compensation data to compensate for any interference in the calculated concentration values.

7. A quantitative analytical method as set forth in claim 6 wherein each group of wave number points corresponds to a peak value and a base value of absorptivity that provides the largest differential of absorptivity by an ingredient with a minimum of mutual absorption by another ingredient.

8. A quantitative analytical method as set forth in claim 6 further including the steps of determining if the calculated concentration of ingredients is appropriate for the group of wave number points used and if not, selecting a different group of stored wave number points until the appropriate group of wave number points is used to calculate the concentration of the ingredients and providing the concentration of the ingredients.

9. A quantitative analytical method as set forth in claim 6 wherein the wave number points are selected, respectively, within the ranges of 3200 cm$^{-1}$ to 3000 cm$^{-1}$, 2400 cm$^{-1}$ to 1800 cm$^{-2}$, and 1500 cm$^{-1}$ to 1000 cm$^{-1}$.

10. A quantitative analytical method of using spectrometric analysis, in which a sample is irradiated with light, and a plurality of ingredients contained in the sample to be measured are quantitatively determined on the basis of absorptivities at a plurality of appointed wave number points in an absorption spectrum obtained at that time, comprising:

establishing groups of ingredients to be measured suitable to a plurality of kinds of samples to be measured, those groups having ingredients which can be approximately estimated;

determining groups of wave number points corresponding to the respective groups of ingredients;

storing the groups of wave number points;

measuring the value of a sample across an absorption spectrum containing the groups of wave number points;

using one of the groups of wave number points to calculate the concentration of the values of the ingredients in the sample;

compensating for the calculated concentration values by use of a reverse matrix calculation having a vector with a significant linear independency to reduce the effect of mutual interference between ingredients;

determining if the calculated concentration of ingredients is appropriate for the group of wave number points used and if not, selecting a different group of stored wave number points until the appropriate group of wave number points is used to calculate the concentration of the ingredients; and providing the concentration of the ingredients.

11. A quantitative analytical method measuring the ingredients in an exhaust gas of using Fourier Transform infrared spectrometric analysis, in which a sample of an exhaust gas is irradiated with infrared light, and a plurality of ingredients contained in the sample to be measured are quantitatively determined on the basis of absorptivities at a plurality of appointed wave number points in an absorption spectrum obtained at that time, comprising:

establishing separate matrixes for groups of ingredients to be measured suitable to a plurality of kinds of samples to be measured, those groups having ingredients which can be approximately estimated;

determining groups of wave number points corresponding to the respective groups of ingredients;

storing the groups of wave number points;

irradiating a sample of exhaust gas with infrared light;

measuring the absorption values of the sample across an absorption spectrum containing the groups of wave number points;

selecting one of the matrixes and using one of the groups of wave number points to calculate the concentration of the values of the ingredients in the sample;

compensating for the calculated concentration values by use of a reverse matrix calculation having a vector with a significant linear independency to reduce the effect of mutual interference between ingredients;

determining if the calculated concentration of ingredients is appropriate for the group of wave number points used and if not, selecting a different group of stored wave number points until the appropriate group of wave number points is used to calculate the concentration of the ingredients; and providing the concentration of the ingredients.

12. A spectrometric apparatus for determining the constituent elements in an exhaust gas, comprising:

a sample cell for holding a sample of an exhaust gas;

means for irradiating the sample of the exhaust gas with infrared light;

means for providing an interferogram representative of the sample of exhaust gas from the interaction of the infrared light;

means for storing a plurality of matrixes of combinations of known constituent elements based on groups of wave number points;

means for measuring the absorption values of the exhaust gas sample from the interferogram;

means for calculating the concentration values of the constituent elements from the absorption values and one of the stored matrixes;

means for compensating for the calculated concentration values by use of a reverse matrix calculation having a vector with a significant linear independency to reduce the effect of mutual interference between constituent elements;

means for determining if the calculated concentration of constituent elements is appropriate for the matrix used and if not, selecting a different matrix until the appropriate group of wave number points is used to calculate the concentration of the constituent elements; and means for providing the concentration of the constituent elements.

* * * * *